US012746381B2

(12) United States Patent
Dikeman et al.

(10) Patent No.: US 12,746,381 B2
(45) Date of Patent: Sep. 29, 2026

(54) COUPLING APPARATUS FOR INFUSION DEVICE

(71) Applicant: Nexus Medical, LLC, Lenexa, KS (US)

(72) Inventors: W. Cary Dikeman, Lenexa, KS (US); Taylor Wilson, Lee's Summit, MO (US)

(73) Assignee: Nexus Medical, LLC, Lenexa, KS (US)

( * ) Notice: Subject to any disclaimer, the term of this patent is extended or adjusted under 35 U.S.C. 154(b) by 740 days.

(21) Appl. No.: 18/298,121

(22) Filed: Apr. 10, 2023

(65) Prior Publication Data

US 2023/0241366 A1 Aug. 3, 2023

Related U.S. Application Data

(63) Continuation of application No. 17/573,769, filed on Jan. 12, 2022, now Pat. No. 11,690,993.

(51) Int. Cl.

| | |
|---|---|
| ***A61M 39/10*** | (2006.01) |
| ***A61M 5/145*** | (2006.01) |
| ***A61M 39/22*** | (2006.01) |

(52) U.S. Cl.

CPC .......... *A61M 39/10* (2013.01); *A61M 5/1452* (2013.01); *A61M 39/22* (2013.01); *A61M 2039/1038* (2013.01); *A61M 2039/1088* (2013.01); *A61M 2205/0216* (2013.01)

(58) Field of Classification Search

CPC .. A61M 2039/1072; A61M 2039/1088; A61M 2039/2406; A61M 2039/2433; A61M 39/26; A61M 5/1452; A61M 2039/267; A61M 39/10

See application file for complete search history.

(56) References Cited

U.S. PATENT DOCUMENTS

| | | | | |
|---|---|---|---|---|
| 2010/0249723 A1* | 9/2010 | Fangrow, Jr. | ......... | A61M 39/10 604/247 |
| 2010/0298782 A1 | 11/2010 | Winsor et al. | | |
| 2012/0130352 A1 | 5/2012 | Naftalovitz et al. | | |
| 2019/0001114 A1 | 1/2019 | Fangrow | | |

FOREIGN PATENT DOCUMENTS

| | | |
|---|---|---|
| TW | I748600 B | 12/2021 |

OTHER PUBLICATIONS

European Patent Application 23151384.7, Communication pursuant to Article 94(3) EPC, issued Oct. 1, 2025.
Canadian Patent Application 3,186,085 Examination Report issued May 3, 2024.
European Patent Application 23151384.7 Extended Search Report issued May 11, 2023.

* cited by examiner

*Primary Examiner* — Deanna K Hall
(74) *Attorney, Agent, or Firm* — Erise IP, P.A.

(57) ABSTRACT

An infusion device for the passage of fluids to or from a patient via a syringe. The infusion device includes a valve assembly and a coupling apparatus. The coupling apparatus comprises a coupler, a first gland, a cannula, a second gland, and an inlet. The coupling apparatus defines a central lumen for the passage of fluids in an open configuration. The inlet may be coupled to a syringe.

20 Claims, 7 Drawing Sheets

COUPLING APPARATUS FOR INFUSION DEVICE

CROSS-REFERENCE TO RELATED APPLICATIONS

This patent application is a continuation application claiming priority benefit, with regard to all common subject matter, of U.S. patent application Ser. No. 17/573,769, filed Jan. 12, 2022, and entitled "COUPLING APPARATUS FOR INFUSION DEVICE," the entirety of which is hereby incorporated by reference into the present application.

BACKGROUND

1. Field

Embodiments of the invention relate generally to pressure-activated infusion devices for the administration of fluids to patients. More specifically, embodiments of the present invention are directed to a coupling apparatus designed to connect a valve assembly to a syringe.

2. Related Art

The use of infusion devices for the administration of parenteral and other fluids to patients is a common practice. A variety of devices for such purposes have been proposed in the past, such as a simple length of tubing having a fitting on one end for making connection with a source of fluid (e.g., a bottle or flexible bag), while the other end is provided with a needle or catheter which may be inserted into the vein of a patient. More commonly, however, specialized infusion devices are provided which include a venous needle (or catheter) at one end and a septum at the other end. In the use of these devices, the needle (or catheter) is inserted into the patient's vein and the device is taped or otherwise affixed to the patient or adjacent equipment. Thereupon, a cannula connected to a liquid supply may be inserted into the free septum end of the device in order to begin fluid therapy. The septum provides a swabbable injection site that can be reused, while the intravenous catheter remains inserted into the patient's vein. A persistent problem with prior infusion devices is referred to as fluid reflux, or the tendency for fluids, such as blood or medication, to be drawn into the infusion apparatus. Fluid reflux can occur in prior art devices, for example, when a gravity supply fluid source is empty, when medication is infused through an adjacent component, or when a cannula is removed from a septum or port. In an attempt to prevent fluid reflux, pressure-activated infusion devices are used.

Prior art pressure-activated infusion devices that reduce blood reflux using a flexible check valve are problematic due to precise coupling of the valve to the infusion device. Coupling of flexible check valves to pressure-activated infusion devices is notoriously difficult due to required alignment of the internal passage with the valve housing. Prior art check valves and associated couplers are also known to shift or "squirm" within the housing, often when the valve is seated in the housing. This inadvertent movement can cause valve misalignment and improper operation. Additionally, prior art infusion devices are problematic due to unexpected levels of fluid reflux caused by compression and decompression of the flexible valves.

There is accordingly a need in the art for improved pressure-activated infusion devices equipped with a specific coupler to properly align and secure the valve component to the pressure-activated infusion device, which reduces or eliminates the possibility of blood reflux and can be reliably manufactured.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

One embodiment comprises a coupling apparatus configured to connect a syringe to a patient via a valve assembly for infusion of fluids. The coupling apparatus comprises a coupler having a central bore, a second gland, a cannula, a first gland, and an inlet. The second gland has a distal segment, a proximal segment, and a proximal cannula lumen, and is entirely received within the central bore of the coupler. The cannula has a distal extension, a medial portion, a proximal extension, and a central lumen therethrough, and the distal extension of the cannula is received within the proximal cannula lumen of the first gland. The first gland has a distal section, a medial section, and a proximal section, and the proximal extension of the cannula is received within both the distal section and the medial section of first gland. The inlet has an inlet flange, a medial rib, a collar, and a central lumen, wherein said inlet flange is received within the central bore of the coupler, and the inlet receives the first gland, the entire cannula, and the proximal segment of the second gland within the central lumen.

One embodiment comprises a system for controlling the flow of liquids to and from a patient, comprising a valve assembly and a coupling apparatus. The valve assembly comprises a male luer lock fitting and a flow control valve. The coupling apparatus comprises a coupler, a second gland, a cannula, a first gland, and an inlet. The coupler comprises a distal flange and a proximal flange, wherein the distal flange is mechanically coupled to the male luer lock fitting, and the proximal flange is mechanically coupled to the inlet. The second gland comprises a distal segment and a proximal segment, wherein the distal segment operatively engages the proximal flange of the coupler, and the proximal segment operatively engages a distal extension of the cannula. The first gland comprises a distal section and a proximal section, wherein the distal section operatively engages a proximal extension of the cannula, and wherein the proximal section operatively engages the inlet. The inlet comprises an inlet flange defining a lumen, wherein the first gland, the cannula, and the proximal segment of the second gland are received within the lumen of the inlet.

Another embodiment comprises an infusion device configured to connect a syringe to a patient via a valve assembly. The infusion device comprises a coupling apparatus and a central lumen. The coupling apparatus comprises a coupler, a second gland, a cannula, a first gland, and an inlet. The coupler comprises a proximal flange, wherein the proximal flange mechanically engages the inlet and the second gland. The cannula is received within the second gland and within the first gland. The inlet operatively engages the second gland and the first gland. The second gland, the cannula, and the first gland are received within the proximal flange of the coupler and an inlet flange of the inlet.

BRIEF DESCRIPTION OF THE DRAWING FIGURES

Embodiments of the invention are described in detail below with reference to the attached drawing figures, wherein.

Figure 1:
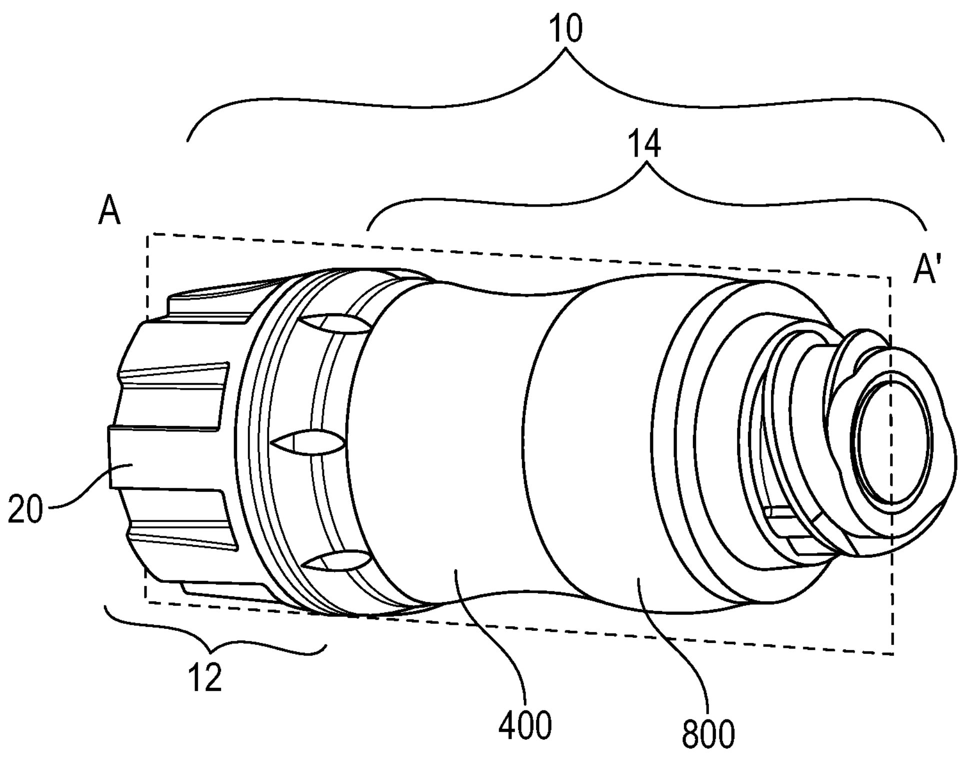
FIG. 1 is a perspective view of a valve assembly constructed in accordance with a first embodiment of the present invention.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of the equivalents to which such claims are entitled.

In this description, references to “one embodiment,” “an embodiment,” or “embodiments” mean that the feature or features being referred to are included in at least one embodiment of the technology. Separate references to “one embodiment,” “an embodiment,” or “embodiments” in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Embodiments of the invention are directed to a coupling apparatus of an infusion device and a coupling system that couples a valve assembly to a syringe. Particularly, the coupling apparatus may operatively connect a pressure-actuated flow control valve to a syringe whereby the connection may regulate infusion of medical liquids into a patient or aspiration of blood from the patient.

Figure 2:
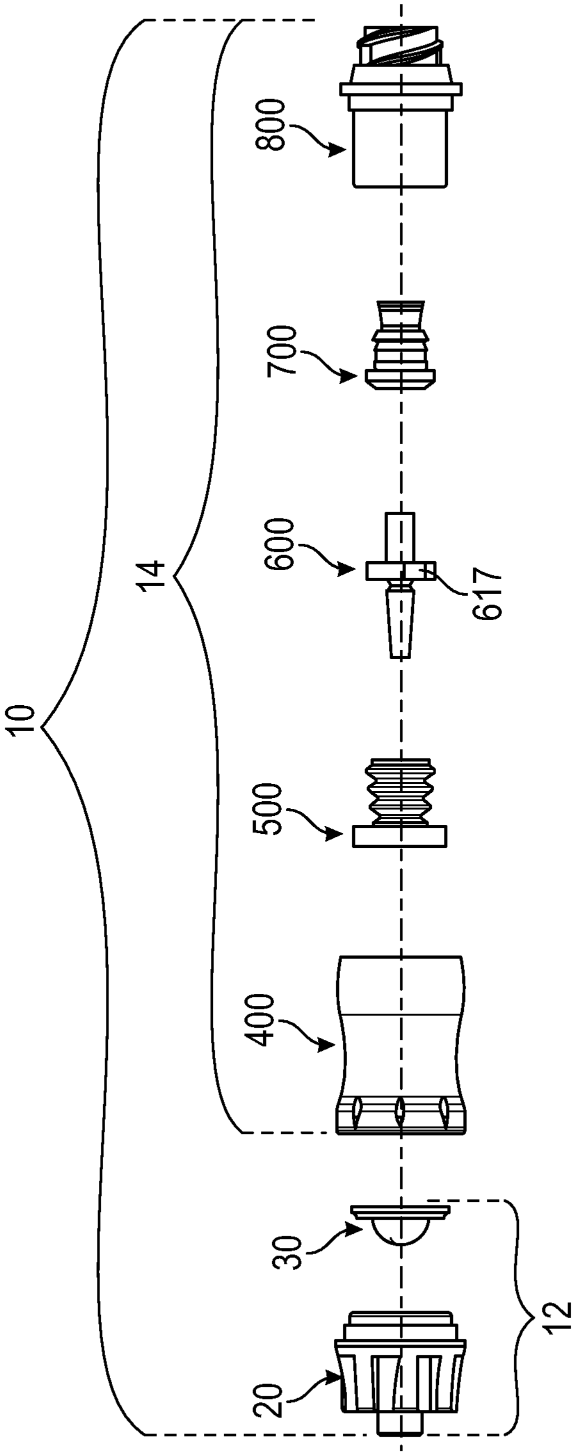
FIG. 2 is an exploded side view of the first embodiment of the valve assembly, particularly showing a male luer lock fitting, a flow control valve, a coupler, a second gland, a cannula, a first gland, and an inlet.

FIG. 1 shows a first embodiment of an infusion device 10. The infusion device 10 may comprise a valve assembly 12 and a coupling apparatus 14. The infusion device 10 may include a male luer lock fitting 20, a coupler 400, and an inlet 800. As can be seen in FIG. 2, the infusion device 10 may also include a flow control valve 30 housed in between the male luer lock fitting 20 and the coupler 400. In some embodiments, flow control valve 30 may be pressure activated, such that it opens and closes based on a particular pressure differential. In some embodiments, flow control valve 30 may be a diaphragm. In some embodiments, flow control valve 30 may be comprised of a medical grade elastomeric material, such as a silicone elastomer. As can be seen in FIG. 2, the coupling apparatus 14 may also include a second gland 500, a cannula 600, and a first gland 700 housed within the coupler 400 and the inlet 800.

Valve assemblies, similar to the valve assembly 12 presented here, may be used in infusion devices. Valve assembly 12 may be similar to the assembly of commonly-owned U.S. Pat. No. 7,967,797, entitled INTRAVASCULAR VALVE COMPONENT WITH IMPROVED VALVE POSITIONING, which is herein incorporated by reference in its entirety.

Figure 3:
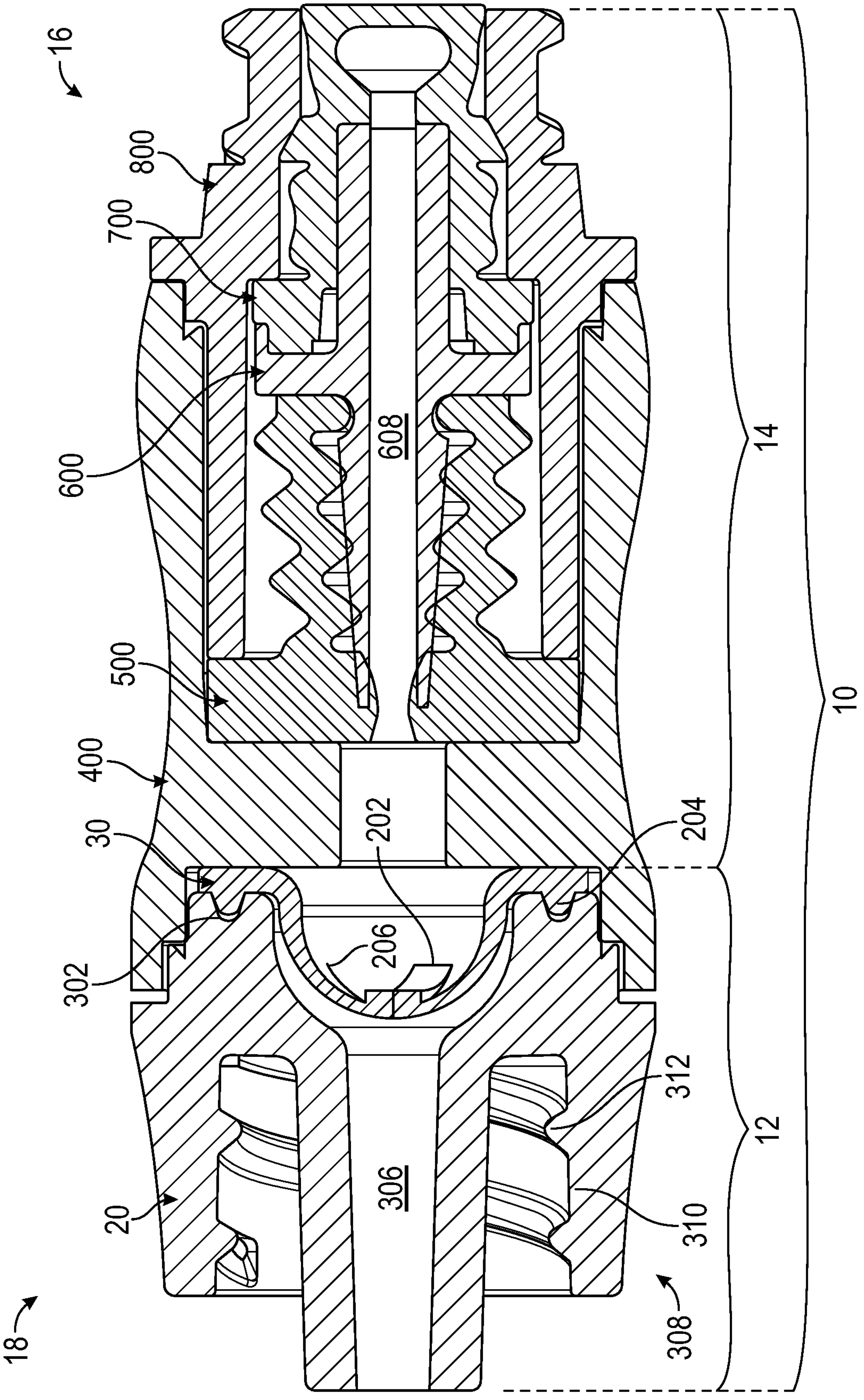
FIG. 3 is a cross-sectional view of the first embodiment of the valve assembly in a coupled configuration.

FIG. 3 illustrates a cross-sectional view of the infusion device 10 in a coupled configuration, in one embodiment. Infusion device 10 comprises a proximal portion 16 and a distal portion 18. The valve assembly 12 is located distally to the coupling apparatus 14. The coupling apparatus further comprises a central lumen 608, defined by the second gland 500, the cannula 600, and the first gland 700. The central lumen 608 provides a flow path for the movement of liquids in either direction through the length of the coupling apparatus 14.

The flow control valve 30, also known as a pressure-activated valve, has a valve surface 202 and a central slit 206. In some embodiments, the valve surface 202 may have a convex form. In some embodiments, the valve surface 202 may have a concave form. The flow control valve 30 provides bidirectional flow control of fluid passing through the device based on pressure. In some embodiments, the flow control valve 30 is designed to selectively prevent fluid flow in the proximal direction. More particularly, the flow control valve 30 prevents proximal flow when an aspiration pressure differential (i.e., where the pressure against the convex surface of the flow control valve 30 is greater than the pressure against the concave surface of the flow control valve 30) across the flow control valve 30 is below a set aspiration amount. The set aspiration amount is generally greater than the venous pressure (relative to atmosphere pressure) of the patient when fluid is not being injected or aspirated through the injection site. Thus, when the flow control valve 30 experiences the typical venous pressure of the patient, the corresponding aspiration pressure differential is less than the set aspiration amount and is not sufficient to open the flow control valve 30. However, when it is desired to aspirate fluid across the flow control valve 30, fluid can be drawn through the injection site by reducing the fluid pressure on a proximal side of the flow control valve 30 (e.g., by drawing fluid with a syringe) so that the aspiration pressure differential exceeds the set aspiration amount. This causes the flow control valve 30 to open in the proximal direction and allow aspiration flow through the central lumen 608. In some embodiments, the flow control valve 30 is designed to selectively prevent fluid flow in the distal direction. More particularly, the flow control valve 30 prevents distal flow when an infusion pressure differential (i.e., where the pressure against the concave surface of the flow control valve 30 is greater than the pressure against the convex surface of the flow control valve 30) across the flow control valve 30 is below a set infusion amount. When an external pressure is applied to a proximal side of the flow control valve 30 (e.g., by injection fluid from a syringe or other fluid supply) and the infusion pressure differential exceeds the set infusion amount, the flow control valve 30 opens in the distal direction to allow infusion flow through a central fluid passageway 306. In some embodiments, flow control valve 30 may be configured so that the set aspiration pressure differential required to open the flow control valve 30 is greater than the set infusion pressure differential required to open the flow control valve 30. In an embodiment, the valve surface 202 includes a valve protrusion 204 on the periphery of the flow control valve 30. Valve protrusion 204 may operatively engage the luer lock fitting 20 by being received within flow valve locking groove 302. Valve protrusion 204 may be an annular ring that ensures the valve is always concentric in the device to ensure proper function. Valve 30 also comprises a ridge band and an apex diminishing wall to establish at what pressure the valve opens and in which direction.

The male luer lock fitting 20 includes the central fluid passageway 306 and a rotatable threaded collar 308. In one embodiment, the central fluid passageway 306 allows for the flow of fluids in either the distal or the proximal direction when the flow control valve 30 is activated. In one embodiment, the central fluid passageway 306 is fluidly coupled to the central lumen 608, wherein the central fluid passageway 306 and the central lumen 608 define the fluid pathway for the infusion device 10. The rotatable threaded collar 308 includes an outer body 310 having an internal threading 312, which is configured to be coupled with another threaded medical device, such as a device having an ISO 594 luer connection.

Figure 4:
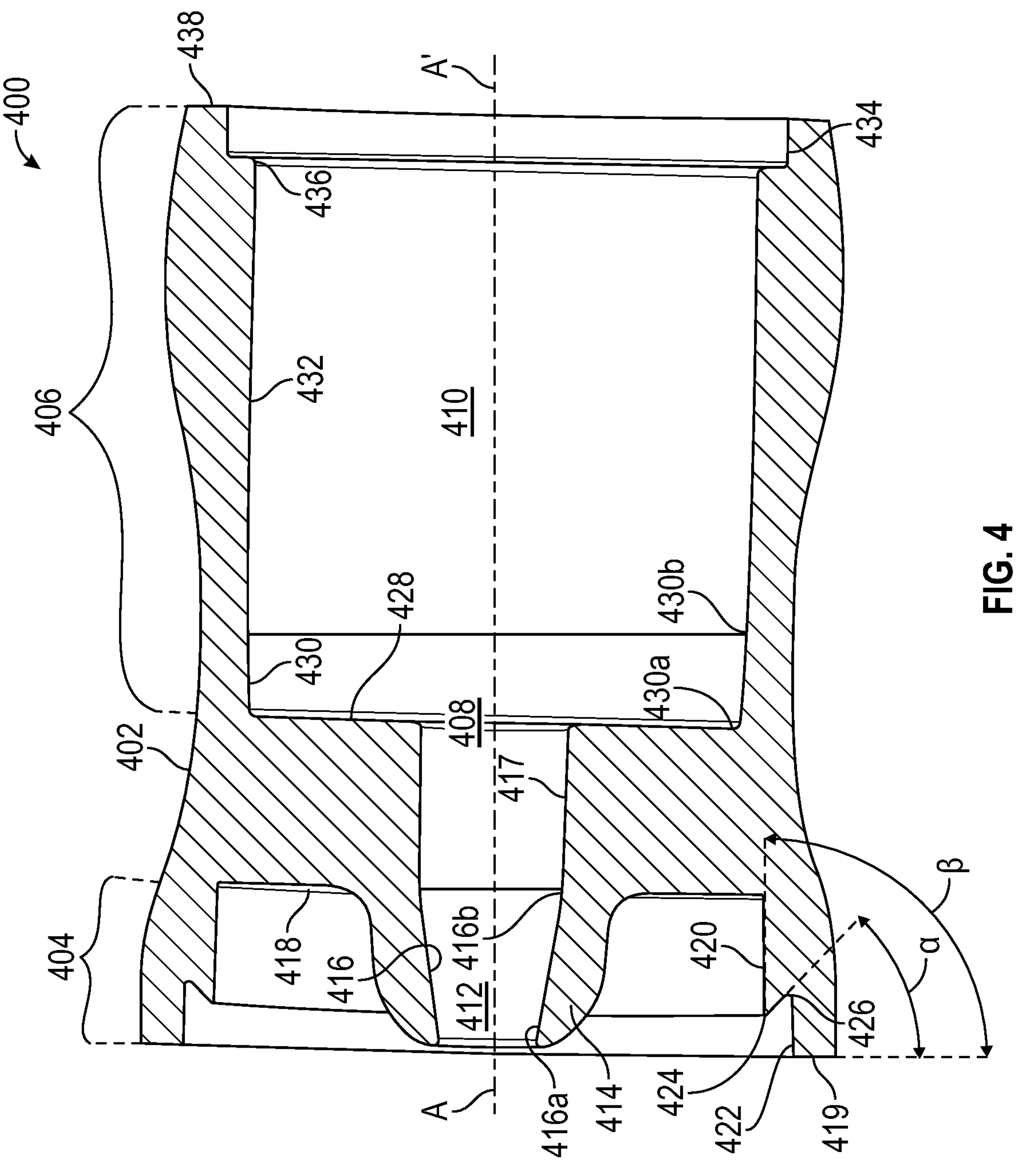
FIG. 4 is a cross-sectional view of an embodiment of the coupler.

Referring now to FIG. 4, a cross-sectional view of the coupler 400 is depicted along the plane A-A'. In one embodiment, the coupler 400 may stabilize the second gland 500 when in the coupled configuration. The coupler 400 may further provide an inward force on the second gland 500 to aid the second gland 500 in the sealing around the cannula 600 when in the coupled configuration. The coupler 400 may further stabilize the flow control valve 30 within the male luer lock fitting 20. In one embodiment, the exterior of the coupler 400 may comprise an ergonomic grip, such as an hourglass shape, for ease of the user who may connect or disconnect the infusion device 10.

In an embodiment, the coupler 400 may comprise an outer wall 402 defining a distal flange 404 and a proximal flange 406. The outer wall 402 may define a central bore 408, which traverses the coupler 400 in the longitudinal direction. The central bore 408 may further comprise a proximal bore section 410 and a distal bore section 412. In one embodiment, the proximal bore section 410 has a wider lumen than the distal bore section 412.

In one embodiment, the distal bore section 412 is defined by a distal axial wall 416 and a distal longitudinal wall 417. In one embodiment, the distal axial wall 416 may be defined by a housing protrusion 414 which extends distally from a valve wall 418. The housing protrusion 414, in one embodiment, may comprise a substantially dome shaped configuration. In some embodiments, the housing protrusion 414 may be configured to prevent collapse of the flow control valve 30 when pressure is applied to the distal side. In one embodiment, the housing protrusion 414 may extend distally between about 0.05 inches to about 0.15 inches from the valve wall 418. In one embodiment, the housing protrusion 414 may extend distally between about 0.09 inches to about 0.11 inches from the valve wall 418. In one embodiment, the distal bore section 412 may not comprise the distal axial wall 416 or the housing protrusion 414. In one embodiment, the distal axial wall 416 may taper radially outwards in the proximal direction. For example, the proximal rim **416*b* of the distal axial wall 416 may have a larger inner diameter than the distal rim 416*a* of the distal axial wall 416. In one embodiment, the inner diameter of the proximal rim 416*b* may be about 60% to about 80% greater than the inner diameter of the distal rim 416*a*. In one embodiment, the inner diameter of the proximal rim 416*b* may be about 65% to about 70% greater than the inner diameter of the distal rim 416*a*. In one embodiment, the inner diameter of the proximal rim 416*b* may be about 68% greater than the inner diameter of the distal rim 416*a***.

In one embodiment, the inner diameter of the distal longitudinal wall 417 may be between about 0.05 inches to about 0.15 inches. In one embodiment, the inner diameter of the distal longitudinal wall 417 may be between about 0.08 inches to about 0.12 inches. In one embodiment, the inner diameter of the distal longitudinal wall 417 may be about 0.1 inches.

In one embodiment, the distal longitudinal wall 417 extends between about 0.05 inches to about 0.15 inches in the longitudinal direction. In one embodiment, the distal longitudinal wall 417 extends between about 0.08 inches to about 0.12 inches in the longitudinal direction. In one embodiment, the distal longitudinal wall 417 extends about 0.1 inches in the longitudinal direction.

In one embodiment, the distal flange 404 may be configured to mechanically couple to the valve assembly 12. In an embodiment, the distal flange 404 may comprise the valve wall 418, wherein the valve wall 418 may operatively engage the flow control valve 30 when in the coupled configuration. In one embodiment, the distal flange 404 may extend distally from the valve wall 418 between about 0.05 inches to about 0.15 inches. In one embodiment, the distal flange 404 may extend distally from the valve wall 418 between about 0.08 inches to about 0.12 inches. In one embodiment, the distal flange 404 may extend distally from the valve wall 418 about 0.1 inches.

In one embodiment, the distal flange 404 may comprise an axial end wall 419. In one embodiment, the distal flange 404 may further comprise a coupler proximal face 420 and a coupler distal face 422, separated by a swage 424 and a swage recess 426. The swage 424 and swage recess 426 may mechanically couple to the male luer lock fitting 20 in the coupled configuration. In one embodiment, a welded configuration, or mechanical coupling is achieved by ultrasonically welding the swage 424 to the male luer lock fitting 20 to form a permanent connection.

In one embodiment, the swage 424 forms an angle alpha between about 35 degrees to about 55 degrees with respect to the axial end wall 419. In one embodiment, the swage 424 forms an angle alpha of between about 40 degrees to about 50 degrees with respect to the axial end wall 419. In one embodiment, the swage 424 forms an angle alpha of about 45 degrees with respect to the axial end wall 419.

In one embodiment, the coupler proximal face 420 and the coupler distal face 422 form an angle beta of between about 80 degrees to about 100 degrees with respect to the axial end wall 419. In one embodiment, the coupler proximal face 420 and the coupler distal face 422 form an angle beta of between about 85 degrees to about 95 degrees with respect to the axial end wall 419. In one embodiment, the coupler proximal face 420 and the coupler distal face 422 form an angle beta of about 89.5 degrees with respect to the axial end wall 419.

In one embodiment, the coupler distal face 422 may form an inner diameter of between about 0.3 inches to about 0.5 inches. In one embodiment, the coupler distal face 422 may form an inner diameter of between about 0.35 inches to about 0.4 inches. In one embodiment, the coupler distal face 422 may form an inner diameter of between about 0.37 inches to about 0.38 inches.

In one embodiment, the coupler proximal face 420 may form an inner diameter of between about 0.35 inches to about 0.45 inches. In one embodiment, the coupler proximal face 420 may form an inner diameter of between about 0.39 inches to about 0.42 inches.

In one embodiment, the axial end wall 419 may extend axially from the coupler distal face 422 between about 0.02 inches to about 0.035 inches. In one embodiment, the axial end wall 419 may extend axially from the coupler distal face 422 between about 0.026 inches to about 0.03 inches. In one embodiment, the axial end wall 419 may extend axially from the coupler distal face 422 about 0.028 inches.

In one embodiment, the proximal flange 406 may comprise a gland wall 428, a proximal axial wall 430, an inlet housing 432, a proximal inlet housing 434, a proximal swage 436, and a proximal rim 438 defining the proximal bore section 410.

In one embodiment, the gland wall 428 and the proximal axial wall 430 may be configured to operatively engage a second gland coupler wall 524 and a second gland distal longitudinal wall 528, respectively, of the second gland 500 when in the coupled configuration. In one embodiment, the gland wall 428 may extend axially from the proximal axial wall 430 between about 0.05 inches to about 0.15 inches. In one embodiment, the gland wall 428 may extend axially from the proximal axial wall 430 between about 0.08 inches to about 0.12 inches. In one embodiment, the gland wall 428 may extend axially from the proximal axial wall 430 about 0.1 inches.

The outer diameter of the gland wall 428 may be defined by a distal portion **430*a* of the proximal axial wall 430. In one embodiment, the inner diameter of the distal portion 430*a* of the proximal axial wall 430 may be smaller than the inner diameter of a proximal portion 430*b* of the proximal axial wall 430. In one embodiment, the inner diameter of the distal portion 430*a* may be about the same inner diameter as the proximal portion 430*b*. In one embodiment, inner diameter of the distal portion 430*a* may be between about 96% to about 100% the inner diameter of the proximal portion 430*b*. In one embodiment, the inner diameter of the distal portion 430*a* may be about 98% the inner diameter of the proximal portion 430*b*. In one embodiment, the inlet housing 432 may extend proximally from the gland wall 428, thereby lacking the proximal axial wall 430** altogether.

In one embodiment, the inlet housing 432 and proximal inlet housing 434 may be separated by the proximal swage 436. In one embodiment, at least one or more of the inlet housing 432, proximal inlet housing 434, and the proximal swage 436 may be configured to mechanically couple to the inlet 800 when in the coupled configuration.

In one embodiment, the proximal flange 406 may extend proximally from the gland wall 428 between about 0.3 inches to about 0.5 inches. In one embodiment, the proximal flange 406 may extend proximally from the gland wall 428 between about 0.35 inches to about 0.45 inches. In one embodiment, the proximal flange 406 may extend proximally from the gland wall 428 about 0.41 inches.

In one embodiment, the inlet housing 432 defines an inner diameter of between about 0.3 inches to about 0.4 inches. In one embodiment, the inlet housing 432 defines an inner diameter of between about 0.32 inches to about 0.36 inches. In one embodiment, the inlet housing 432 defines an inner diameter of about 0.34 inches.

In one embodiment, the proximal inlet housing 434 defines an inner diameter of between about 0.3 inches to about 0.45 inches. In one embodiment, the proximal inlet housing 434 defines an inner diameter of between about 0.35 inches to about 0.4 inches. In one embodiment, the proximal inlet housing 434 defines an inner diameter of about 0.38 inches. In one embodiment, the proximal inlet housing 434 defines a diameter larger than the diameter defined by the inlet housing 432. In one embodiment, the inlet housing 432 defines a diameter larger than the diameter defined by the distal longitudinal wall 417. In one embodiment, the coupler proximal face 420 defines a diameter slightly larger than the diameter defined by the inlet housing 432 and a diameter slightly smaller than the diameter defined by the proximal inlet housing 434. In one embodiment, the coupler distal face 422 defines a diameter slightly larger than the diameter defined by the proximal inlet housing 434.

In one embodiment, the proximal inlet housing 434 extends proximally from the proximal swage 436 between about 0.01 inches to about 0.05 inches. In one embodiment, the proximal inlet housing 434 extends proximally from the proximal swage 436 about 0.03 inches.

In one embodiment, the proximal swage 436 is configured to mechanically couple to the inlet 800 in the coupled configuration. In one embodiment, a welded configuration, or mechanical coupling is achieved by ultrasonically welding the proximal swage 436 to the inlet 800.

In one embodiment, the proximal flange 406 further comprises a proximal rim 438. In one embodiment, the proximal rim 438 may mechanically engage the inlet 800 when in the coupled configuration. In one embodiment, the proximal rim 438 may extend axially from the proximal inlet housing 434 between about 0.015 inches to about 0.04 inches. In one embodiment, the proximal rim 438 may extend axially from the proximal inlet housing 434 between about 0.02 inches to about 0.03 inches. In one embodiment, the proximal rim 438 may extend axially from the proximal inlet housing 434 about 0.027 inches.

In one embodiment, the proximal flange 406 extends proximally from the gland wall 428 about 0.41 inches, and proximal rim 438 extends outwardly from proximal inlet housing 434 about 0.027 inches, the proximal inlet housing 434 extends distally from the proximal rim about 0.03 inches, the proximal swage 436 extends axially from the proximal inlet housing 434 about 0.02 inches, the inlet housing 432 extends distally from the proximal swage 436 about 0.312 inches, the proximal axial wall 430 extends axially from the inlet housing 432 about 0.058 inches, the gland wall 428 extends axially from the proximal axial wall 430 about 0.107 inches, the distal longitudinal wall 417 extends distally from the gland wall 428 about 0.107 inches, the distal axial wall 416 extends distally from the distal longitudinal wall 417 about 0.103 inches, the valve wall 418 extends axially from the housing protrusion about 0.071 inches, the coupler proximal face 420 extends distally from the valve wall 418 about 0.077 inches, the swage 424 extends from the coupler proximal face 420 to the swage recess 426 at about 0.018 inches, the coupler distal face 422 extends distally from the swage recess 426 about 0.04 inches, and the axial end wall 419 extends axially from the coupler distal face 422 about 0.028 inches.

In some embodiments, the coupler 400 may comprise an elastomeric medical grade synthetic resin material. In some embodiments, the coupler 400 may comprise a medical grade rigid or semirigid synthetic resinous material suitable for supporting an operable connection, such as, for example, polyvinyl chloride or polycarbonate. In some embodiments, the coupler 400 provides an ultrasonically weldable interface for attaching the male luer lock fitting 20 to the inlet 800.

Figure 5:
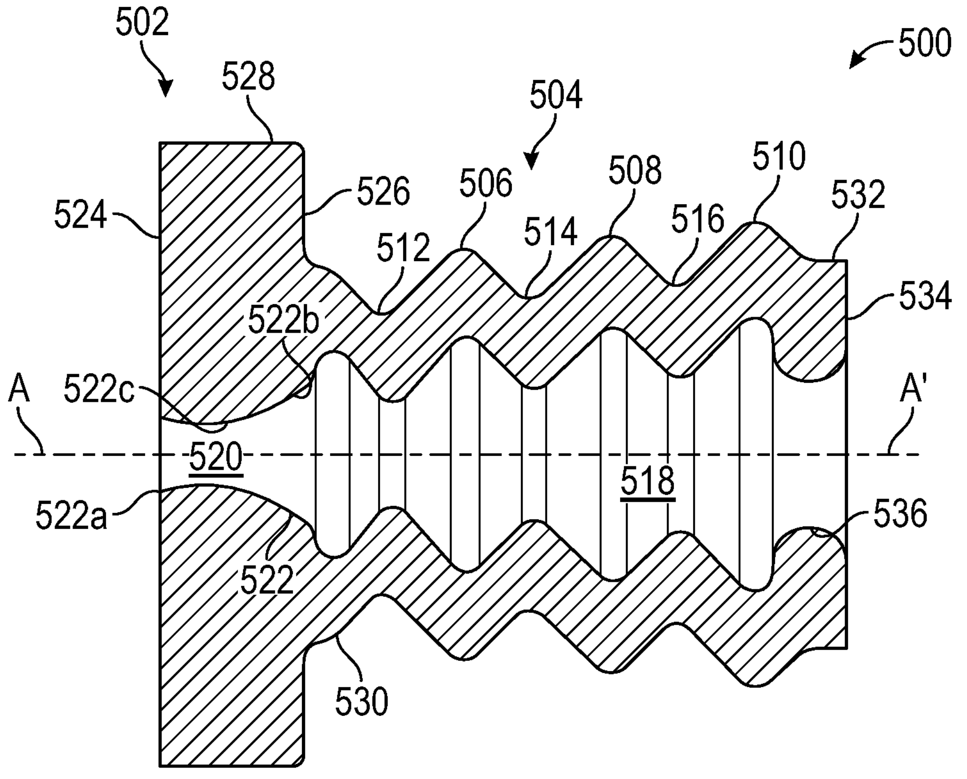
FIG. 5 is a cross-sectional view of an embodiment of the second gland.

Referring now to FIG. 5, a cross-sectional view of the second gland 500, also referred to as a lower septum, is depicted along the plane A-A'. In one embodiment, the second gland 500 may provide a proximally-directed force as a syringe is removed from the proximal end of the infusion device 10. In one embodiment, the second gland 500 may include a tapered design which may allow it to compress as a syringe male luer 900 is inserted into the proximal end of the infusion device 10 (see FIG. 9), but return to an original relaxed shape upon removal of the syringe.

The second gland 500 may comprise a distal segment 502 and a proximal segment 504. In one embodiment, the proximal segment 504 may comprise a plurality of circumferential protrusions and circumferential recesses. In some embodiments, the proximal segment 504 may comprise one, two, three or four, or more circumferential protrusions and/or recesses. For example, the proximal segment 504 may comprise a first circumferential protrusion 530, a second circumferential protrusion 506, a third circumferential protrusion 508, and a fourth circumferential protrusion 510. The proximal segment 504 may also include a plurality of recesses disposed between the plurality of protrusions 530, 506, 508, 510. For example, a first circumferential recess 512 may be disposed between the first circumferential protrusion 530 and the second circumferential protrusion 506. In one example, a second circumferential recess 514 may be disposed between the second circumferential protrusion 506 and the third circumferential protrusion 508. In one example, a third circumferential recess 516 may be disposed between the third circumferential protrusion 508 and the fourth circumferential protrusion 510.

In one embodiment, the plurality of circumferential protrusions 530, 506, 508, 510 may comprise varied internal diameters. In one example, the plurality of circumferential protrusions may increase in diameter in the proximal direction. For instance, in one embodiment, the second circumferential protrusion 506 may comprise a larger internal diameter than the first circumferential protrusion 530. In one embodiment, the third circumferential protrusion 508 may comprise a larger internal diameter than the second circumferential protrusion 506. In one embodiment, the fourth circumferential protrusion 510 may comprise a larger internal diameter than the third circumferential protrusion 508.

In one embodiment, the first circumferential protrusion 530 may comprise an internal diameter of between about 0.05 inches to about 0.15 inches. In one embodiment, the first circumferential protrusion 530 may comprise an internal diameter of between about 0.08 inches to about 0.12 inches. In one embodiment, the first circumferential protrusion 530 may comprise an internal diameter of about 0.1 inches.

In one embodiment, the second circumferential protrusion 506 may comprise an internal diameter of between about 0.05 inches to about 0.15 inches. In one embodiment, the second circumferential protrusion 506 may comprise an internal diameter of between about 0.09 inches to about 0.13 inches. In one embodiment, the second circumferential protrusion 506 may comprise an internal diameter of about 0.12 inches.

In one embodiment, the third circumferential protrusion 508 may comprise an internal diameter of between about 0.08 inches to about 0.17 inches. In one embodiment, the third circumferential protrusion 508 may comprise an internal diameter of between about 0.1 inches to about 0.15 inches. In one embodiment, the third circumferential protrusion 508 may comprise an internal diameter of about 0.13 inches.

In one embodiment, the fourth circumferential protrusion 510 may comprise an internal diameter of between about 0.09 inches to about 0.18 inches. In one embodiment, the fourth circumferential protrusion 510 may comprise an internal diameter of between about 0.12 inches to about 0.16 inches. In one embodiment, the fourth circumferential protrusion 510 may comprise an internal diameter of about 0.14 inches.

In one embodiment, the plurality of circumferential recesses may additionally or alternatively comprise varied internal diameters. In one example, the plurality of circumferential recesses may increase in diameter in the proximal direction. For instance, in one embodiment, the second circumferential recess 514 may comprise a larger internal diameter than the first circumferential recess 512. In one embodiment, the third circumferential recess 516 may comprise a larger internal diameter than the second circumferential recess 514.

In one embodiment, the first circumferential recess 512 may comprise an internal diameter of between about 0.02 inches to about 0.08 inches. In one embodiment, the first circumferential recess 512 may comprise an internal diameter of between about 0.04 inches to about 0.06 inches. In one embodiment, first circumferential recess 512 may comprise an internal diameter of about 0.056 inches.

In one embodiment, the second circumferential recess 514 may comprise an internal diameter of between about 0.03 inches to about 0.11 inches. In one embodiment, the second circumferential recess 514 may comprise an internal diameter of between about 0.05 inches to about 0.09 inches. In one embodiment, the second circumferential recess 514 may comprise an internal diameter of about 0.07 inches.

In one embodiment, the third circumferential recess 516 may comprise an internal diameter of between about 0.05 inches to about 0.12 inches. In one embodiment, the third circumferential recess 516 may comprise an internal diameter of between about 0.07 inches to about 0.09 inches. In one embodiment, the third circumferential recess 516 may comprise an internal diameter of about 0.08 inches.

In one embodiment, directly proximal to the proximal-most circumferential protrusion, such as the fourth circumferential protrusion 510, a second gland proximal longitudinal wall 532 may be disposed. The second gland proximal longitudinal wall 532 may extend from the fourth circumferential protrusion 510 proximally along the A-A' axis. In one embodiment, the second gland proximal longitudinal wall 532 may extend from the fourth circumferential protrusion 510 between about 0.01 inches to about 0.03 inches. In one embodiment, the second gland proximal longitudinal wall 532 may extend from the fourth circumferential protrusion 510 between about 0.015 inches to about 0.02 inches. In one embodiment, the second gland proximal longitudinal wall 532 may extend from the fourth circumferential protrusion 510 about 0.019 inches.

In one embodiment, the second gland proximal longitudinal wall 532 may comprise a second gland cannula wall 534 defining a cannula collar 536. In one embodiment, the second gland cannula wall 534 and the cannula collar 536 may operatively engage the cannula 600 when in the coupled configuration. In one embodiment, the cannula collar 536 protrudes inwardly from the second gland proximal longitudinal wall 532, thereby defining a smaller internal diameter. In one embodiment, the cannula collar 536 defines an internal diameter of between about 0.04 inches to about 0.1 inches. In one embodiment, the cannula collar 536 defines an internal diameter of between about 0.06 inches to about 0.09 inches. In one embodiment, the cannula collar 536 defines an internal diameter of about 0.078 inches.

In one embodiment, the plurality of circumferential protrusions, the plurality of circumferential recesses, and the cannula collar 536 together define a proximal cannula lumen 518. In one embodiment, the proximal cannula lumen 518 is configured to receive a portion of the cannula 600 in the coupled configuration. In one embodiment, the proximal cannula lumen 518 comprises variable diameters defined by the internal diameters of the plurality of circumferential protrusions and the plurality of circumferential recesses, as described above. In one embodiment, the proximal cannula lumen 518 is directly adjacent and in cooperation with a distal cannula lumen 520, which is defined by a cannula restriction wall 522. Both the proximal cannula lumen 518 and the distal cannula lumen 520 define a hollow interior of said second gland 500. In one embodiment, the distal cannula lumen 520 has a substantially closed configuration comprising a slit shape defined by the cannula restriction wall 522 when in the relaxed uncoupled state.

In one embodiment, the distal segment 502 of the second gland 500 comprises a second gland coupler wall 524 and a second gland inlet wall 526 separated by a second gland distal longitudinal wall 528. In one embodiment, the second gland distal longitudinal wall 528 may operatively engage the proximal axial wall 430 of the coupler 400 when in the coupled configuration. In one embodiment, the second gland distal longitudinal wall 528 may extend distally from the second gland inlet wall 526 by between about 0.05 inches to about 0.09 inches. In one embodiment, the second gland distal longitudinal wall 528 may extend distally from the second gland inlet wall 526 by between about 0.06 inches to about 0.08 inches. In one embodiment, the second gland distal longitudinal wall 528 may extend distally from the second gland inlet wall 526 by about 0.07 inches.

In one embodiment, the second gland inlet wall 526 may comprise a substantially flat shape. In one embodiment, the second gland inlet wall 526 may comprise a swage on a more external portion. In this embodiment, the swage portion may aid in the operative engagement of the second gland 500 with the inlet 800 when in the coupled configuration.

In one embodiment, the second gland coupler wall 524 may operatively engage the gland wall 428 of the coupler 400 when in the coupled configuration. In one embodiment, the second gland coupler wall 524 extends radially inward from the second gland distal longitudinal wall 528 to the cannula restriction wall 522 by between about 0.12 inches to about 0.18 inches. In one embodiment, the second gland coupler wall 524 extends radially inward from the second gland distal longitudinal wall 528 to the cannula restriction wall 522 by between about 0.14 inches to about 0.16 inches. In one embodiment, the second gland coupler wall 524 extends radially inward from the second gland distal longitudinal wall 528 to the cannula restriction wall 522 by about 0.15 inches.

In one embodiment, the cannula restriction wall 522 defines an interior opening in which the distal opening **522*a* may be smaller in diameter than the proximal opening 522*b*. In one embodiment, the distal opening 522*a* may define a diameter that is between about 50-70% of the diameter of the proximal opening 522*b*. In one embodiment, the distal opening 522*a* may define a diameter that is between about 60-80% of the diameter of the proximal opening 522*b*. In one embodiment, the distal opening 522*a* may define a diameter that is about 66% of the diameter of the proximal opening 522*b***.

In one embodiment, a medial opening **522*c* defines a section of the cannula restriction wall 522 connecting the distal opening 522*a* and the proximal opening 522*b*. In one embodiment, the diameter of the medial opening 522*c* is between about 60-80% of the diameter of the distal opening 522*a*. In one embodiment, the diameter of the medial opening 522*c* is about 70% of the diameter of the distal opening 522*a*. In one embodiment, the cannula restriction wall 522 may extend radially outward in the proximal direction between the distal opening 522*a* and the proximal opening 522*b* and no distinct medial opening 522*c*** is present.

In one embodiment, the second gland cannula wall 534 extends from the cannula collar 536 to the second gland proximal longitudinal wall 532 a distance of about 0.045 inches, the second gland proximal longitudinal wall 532 extends distally from the second gland cannula wall 534 about 0.019 inches, the fourth circumferential protrusion 510 extends axially from the second gland proximal longitudinal wall 532 about 0.024 inches, the third circumferential recess 516 extends axially from the fourth circumferential protrusion 510 about 0.038 inches, the third circumferential protrusion 508 extends axially from the third circumferential recess 516 about 0.031 inches, the second circumferential recess 514 extends axially from the third circumferential protrusion 508 about 0.041 inches, the second circumferential protrusion 506 extends axially from the second circumferential recess 514 about 0.031 inches, the first circumferential recess 512 extends axially from the second circumferential protrusion 506 about 0.041 inches, the first circumferential protrusion 530 extends axially from the first circumferential recess 512 about 0.024 inches, the second gland inlet wall 526 extends axially from the first circumferential protrusion 530 about 0.052 inches, the second gland distal longitudinal wall 528 extends distally from the second gland inlet wall 526 about 0.071 inches, and the second gland coupler wall 524 extends axially from the second gland distal longitudinal wall 528 about 0.147 inches.

In some embodiments, the second gland 500 may comprise a resilient and/or compressible material. In one embodiment, the second gland 500 may comprise a silicone elastomer with silica filler. In one embodiment, the second gland 500 may comprise a silicone with silica filler that is free of natural rubber, latex, or mercaptobenzimidazol.

Figure 6:
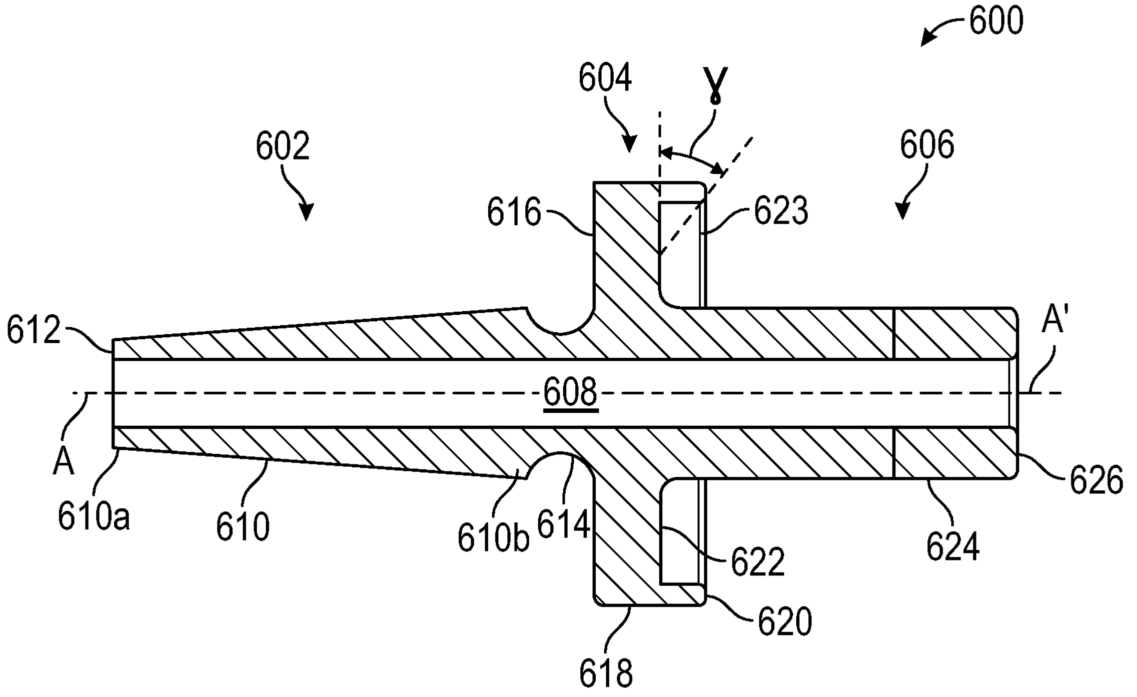
FIG. 6 is a cross-sectional view of an embodiment of the cannula.

Referring to FIG. 6, a cross-sectional view of the cannula 600 is depicted along the plane A-A'. In one embodiment, the cannula 600 may provide a fluid path from the first gland 700 through the second gland 500. In one embodiment, the cannula 600 may be slightly displaced in the distal direction when a syringe male luer 900 is connected to the coupling apparatus 14 (see FIG. 9). The cannula 600 may be designed to allow it to maintain a substantially straight fluid path upon insertion of or removal of a syringe.

In one embodiment, the cannula 600 comprises a distal extension 602 and a proximal extension 606 protruding in opposite directions from a medial portion 604. The cannula 600 may be referred to as a dual barb cannula. The distal extension 602, medial portion 604, and the proximal extension 606 may define a central lumen 608 therethrough. The design of the cannula 600 is configured to distribute the insertion distance of a syringe male luer 900 across both the second gland 500 and the first gland 700 while maintaining an unaltered straight fluid path (see FIG. 9). In some embodiments, the insertion distance of the syringe male luer may be about 0.225 inches. The proximal extension 606 is similar in size to the first gland 700 to limit compression of the first gland 700, thereby preventing premature opening of the slit 766. The medial portion 604 additionally comprises a proximal side with a cupping feature, as will be further described below, to help stabilize first gland 700. The distal extension 602 is tapered and includes locking notch 617 to ensure the second gland 500 remains secured to the cannula 600 during compression.

In one embodiment, the central lumen 608 may comprise an opening that may be between about 0.02 inches to about 0.06 inches in diameter. In one embodiment, the central lumen 608 may comprise an opening that may be between about 0.03 inches to about 0.05 inches in diameter. In one embodiment, the central lumen 608 may comprise an opening that may be about 0.04 inches in diameter.

In one embodiment, the cannula axial wall 610 may taper radially outward in the proximal direction. For example, a distal segment 610*a* of the cannula axial wall 610 may define a smaller outer diameter than a proximal segment 610*b* of the cannula axial wall 610. In one embodiment, the distal segment 610*a* may define an outer diameter of between about 50% to about 70% of the outer diameter of the proximal segment 610*b*. In one embodiment, the distal segment 610*a* may define an outer diameter of between about 55% to about 65% of the outer diameter of the proximal segment 610*b*. In one embodiment, the distal segment 610*a* may define an outer diameter of about 60% of the outer diameter of the proximal segment 610*b*. In some embodiments, the inner diameter of the proximal segment 610*b* and the distal segment 610*a* are substantially the same.

The tapering of the distal extension 602 may enhance the operative connection of the cannula 600 and the second gland 500. In one embodiment, the cannula axial wall 610 may be received within the proximal cannula lumen 518 of the second gland 500, when in the coupled configuration.

The distal extension 602 may further comprise a cannula recess 614 adjacent to the proximal segment 610*b* of the cannula axial wall 610. In one embodiment, the cannula recess 614 may define a decreased outer diameter to that of the proximal segment 610*b*, such that the cannula collar 536 of the second gland 500 may be received within the cannula recess 614 when in the coupled configuration. In one embodiment, the cannula recess 614 may comprise an outer diameter between about 60% to about 80% of the outer diameter of the proximal segment 610*b*. In one embodiment, the cannula recess 614 may comprise an outer diameter between about 65 to about 75% of the outer diameter of the proximal segment 610*b*. In one embodiment, the cannula recess 614 may comprise an outer diameter of about 70% of the outer diameter of the proximal segment 610*b*.

In one embodiment, the medial portion 604 comprises a second gland wall 616 and a medial wall 618. The second gland wall 616 may operatively engage the second gland cannula wall 534 when in the coupled configuration. In one embodiment, the medial wall 618 defines an outer diameter of between about 0.1 inches to about 0.3 inches. In one embodiment, the medial wall 618 defines an outer diameter of between about 0.15 inches to about 0.25 inches.

In one embodiment, the medial wall 618 may comprise a notch 617 on an exterior portion (see FIG. 2). In one embodiment, the notch 617 may comprise a flat portion of the otherwise round medial wall 618. In one embodiment, the notch 617 may be substantially flat. In one embodiment, the notch 617 may be between about 0.02 inches to about 0.06 inches tangentially. In one embodiment, the notch 617 may be between about 0.03 inches to about 0.05 inches tangentially. In one embodiment, the notch 617 may be about 0.04 inches tangentially.

In one embodiment, the medial wall 618 may comprise a first gland swage 620 defining a first gland wall 622. The first gland wall 622 may be configured to receive the first gland 700 when in the coupled configuration. In one embodiment, the first gland swage 620 extends proximally from the first gland wall 622 between about 0.01 inches to about 0.05 inches. In one embodiment, the first gland swage 620 extends proximally from the first gland wall 622 between about 0.02 inches to about 0.04 inches. In one embodiment, the first gland swage 620 extends proximally from the first gland wall 622 about 0.03 inches.

In one embodiment, the first gland wall 622 extends axially from a proximal flange wall 624 between about 0.01 inches to about 0.09 inches. In one embodiment, the first gland wall 622 extends axially from the proximal flange wall 624 between about 0.03 inches to about 0.07 inches. In one embodiment, the first gland wall 622 extends axially from the proximal flange wall 624 about 0.05 inches.

In one embodiment, the first gland swage 620 further comprises a swage rim 623 which forms an angle gamma with respect to the first gland wall 622. The swage rim 623 may be configured to operatively engage a first axial face 716 of the first gland 700 when in the coupled configuration. In one embodiment, the angle gamma is between about 30 degrees to about 50 degrees. In one embodiment, the angle gamma is between about 35 degrees to about 45 degrees. In one embodiment, the angle gamma is about 41 degrees.

In one embodiment, the proximal extension 606 may comprise the proximal flange wall 624 extending in the proximal direction from the first gland wall 622. The proximal flange wall 624 may be configured to operatively engage the first gland 700 when in the coupled configuration. In one embodiment, the proximal flange wall 624 may define an outer diameter of between about 0.05 inches to about 0.15 inches. In one embodiment, the proximal flange wall 624 may define an outer diameter of between about 0.08 inches to about 0.12 inches. In one embodiment, the proximal flange wall 624 may define an outer diameter of about 0.1 inches.

In one embodiment, the proximal flange wall 624 may comprise a proximal rim 626 at the proximalmost end which may extend in the transverse direction. The proximal rim 626 may be configured to operatively engage a cannula restriction face 752 of the first gland 700 when in the coupled configuration. In one embodiment, the proximal rim 626 may extend inwardly from the proximal flange wall 624 between about 0.01 inches to about 0.05 inches. In one embodiment, the proximal rim 626 may extend inwardly from the proximal flange wall 624 between about 0.02 inches to about 0.04 inches. In one embodiment, the proximal rim 626 may extend inwardly from the proximal flange wall 624 about 0.03 inches.

In one embodiment, the proximal rim 626 extends axially from the proximal flange wall 624 about 0.03 inches, the proximal flange wall 624 extends distally from the proximal rim 626 about 0.193 inches, the first gland wall 622 extends axially from the proximal flange wall 624 about 0.05 inches, the distance from the first gland wall 622 to the swage rim 623 is about 0.023 inches, the swage rim 623 rim extends axially from the medial wall 618 about 0.007 inches, the medial wall extends distally from the swage rim 623 about 0.055 inches, the second gland wall 616 extends axially from the medial wall 618 about 0.067 inches, the cannula axial wall 610 extends axially from the cannula recess 614 about 0.24 inches, the distal rim 612 extends axially from the cannula axial wall 610 about 0.007 inches, and the distal rim 612 connects to the proximal rim 626 via the central lumen 608 which defines a distance of about 0.52 inches.

In some embodiments, the cannula 600 may comprise an elastomeric medical grade synthetic resin material. In some embodiments, the cannula 600 may comprise a medical grade rigid or semirigid synthetic resinous material suitable for supporting an operable connection, such as, for example, polyvinyl chloride or polycarbonate. In some embodiments, cannula 600 may comprise rigid polycarbonate.

Figure 7:
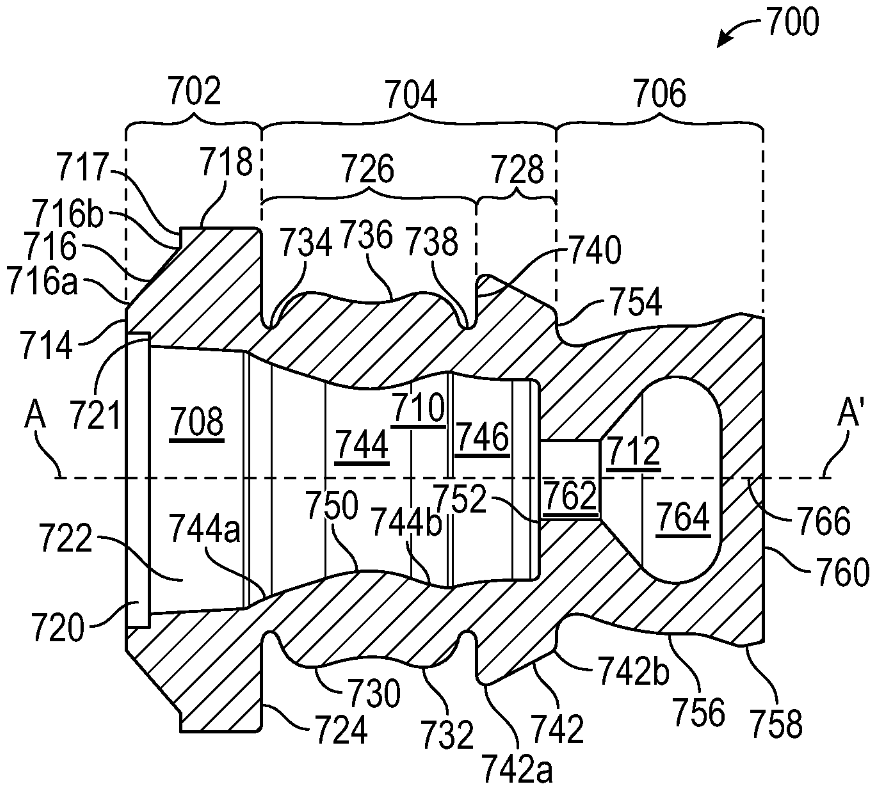
FIG. 7 is a cross-sectional view of an embodiment of the first gland.

Referring to FIG. 7, a cross-sectional view of the first gland 700, also referred to as an upper septum, is depicted along the plane A-A'. In one embodiment, the first gland 700 may establish a closed seal around the proximal end of the infusion device 10 when the infusion device 10 is not being accessed by a syringe. This seal may prevent potential contaminates from entering the infusion device 10. The proximal end of first gland 700 comprises a slit 766. In some embodiments, slit 766 may be a self-opening slit design to prevent the cannula 600 from passing through the slit 766, as will be further described herein.

The first gland 700 may comprise a distal section 702, a medial section 704, and a proximal section 706. The distal section 702 may be configured to operatively engage the cannula 600 and the inlet 800 when in the coupled configuration. In one embodiment, the distal section may comprise a distal face 714, a first axial face 716, a proximal face 717, a first gland longitudinal wall 718, and a first axial wall 724 which define a distal lumen 708.

In one embodiment, the distal face 714 operatively engages the first gland wall 622 of the cannula 600 when in the coupled configuration. In one embodiment, the distal face 714 extends axially from a first distal lumen wall 720 between about 0.015 inches to about 0.03 inches. In one embodiment, the distal face 714 extends axially from the first distal lumen wall 720 between about 0.02 inches to about 0.028 inches. In one embodiment, the distal face 714 extends axially from the first distal lumen wall 720 about 0.024 inches.

In one embodiment, the first axial face 716 may extend radially outwards in the proximal direction and connect the distal face 714 to the proximal face 717, such that a distal portion 716*a* of the first axial face 716 may define a smaller outer diameter than a proximal portion 716*b* of the first axial face 716. In one embodiment, the distal portion 716*a* may define an outer diameter of between about 65% to about 80% of the outer diameter of the proximal portion 716*b*. In one embodiment, the distal portion 716*a* may define an outer diameter of between about 70% to about 75% of the outer diameter of the proximal portion 716*b*. In one embodiment, the distal portion 716*a* may define an outer diameter of about 74% of the outer diameter of the proximal portion 716*b*. In one embodiment, the first axial face 716 may be configured to operatively engage the swage rim 623 of the cannula 600 when in the coupled configuration.

In one embodiment, the proximal face 717 extends axially from the proximal portion 716*b* and is configured to operatively engage the first gland swage 620 of the cannula 600 when in the coupled configuration. In one embodiment, the proximal face 717 extends axially from the proximal portion 716*b* between about 0.005 inches to about 0.015 inches. In one embodiment, the proximal face 717 extends axially from the proximal portion 716*b* between about 0.008 inches to about 0.012 inches. In one embodiment, the proximal face 717 extends axially from the proximal portion 716*b* about 0.01 inches.

In one embodiment, the first gland longitudinal wall 718 may extend proximally from the proximal face 717. In one embodiment, the first gland longitudinal wall 718 may connect the proximal face 717 to the first axial wall 724. In one embodiment, the first axial wall 724 may extend axially from the first gland longitudinal wall 718. In one embodiment, the first axial wall 724 may operatively engage the inlet 800 when in the coupled configuration.

In one embodiment, the distal lumen 708 comprises the first distal lumen wall 720 and a second distal lumen wall 722. In one embodiment, the first distal lumen wall 720 defines a larger inner diameter than the second distal lumen wall 722. In one embodiment, the first distal lumen wall 720 may have an inner diameter of about 105% to about 135% the inner diameter of the second distal lumen wall 722. In one embodiment, the first distal lumen wall 720 may have an inner diameter of about 110% to about 120% the inner diameter of the second distal lumen wall 722. In one embodiment, the first distal lumen wall 720 may have an inner diameter of about 115% the inner diameter of the second distal lumen wall 722. In one embodiment, the distal lumen 708 is configured to receive a portion of the cannula 600 when in the coupled configuration.

In one embodiment, the medial section 704 may comprise a first projection 726 and second projection 728. In one embodiment, the first projection 726 may comprise one or more of a first bulge 730 and a second bulge 732. In one embodiment, the first projection 726 may further comprise one or more of a first recess 734, a second recess 736, and a third recess 738. In one embodiment, the first recess 734 and the third recess 738 may define a smaller outer diameter of medial section 704 than the second recess 736. In one embodiment, the second recess 736 may be disposed between the first bulge 730 and the second bulge 732. In one embodiment, the first bulge 730 and the second bulge 732 define a similar outer diameter. In one embodiment, the first bulge 730 and the second bulge 732 may define a different outer diameter. In one embodiment, the first projection 726 comprises the first bulge 730 disposed between the first recess 734 and the second recess 736.

In one embodiment, the medial section 704 may define a medial lumen 710. In one embodiment, the medial lumen 710 may comprise one or more of a first luminal segment 744 and a second luminal segment 746. In one embodiment, the first projection 726 may define the first luminal segment 744. The first luminal segment 744, in an embodiment, may comprise an intruding bulge 750. In this embodiment, the intruding bulge 750 may define an inner diameter that is smaller than the proximal segment 744*b* and/or distal segment 744*a* of the first luminal segment 744. In another embodiment, the intruding bulge 750 may define an inner diameter that is larger than the proximal segment 744*b* and/or distal segment 744*a* of the first luminal segment 744.

In another embodiment, the intruding bulge 750 may define an inner diameter that is similar to the proximal segment 744*b* and/or distal segment 744*a* of the first luminal segment 744.

In one embodiment, the distal lumen 708 may define an inner diameter that is similar to the inner diameter of the medial lumen 710. In one embodiment, the distal lumen 708 may define an inner diameter that is greater than the inner diameter of the medial lumen 710.

In one embodiment, the second projection 728 may comprise a second axial wall 740, a second axial face 742, and a third axial wall 754. In one embodiment, the second axial wall 740 may extend axially from the third recess 738. In another embodiment, the second axial wall 740 may extend axially from the second recess 736. In one embodiment, the second axial wall 740 may define an outer diameter greater than that of the first bulge 730 and/or the second bulge 732. In one embodiment, the second axial wall 740 may define an outer diameter similar to that of the first bulge 730 and/or the second bulge 732.

In one embodiment, the second axial face 742 may taper radially inwards in the proximal direction. For example, the proximal segment 742*b* of the second axial face 742 may have a smaller outer diameter than the distal segment 742*a* of the second axial face 742. In one embodiment, the distal segment 742*a* of the second axial face 742 may comprise an outer diameter of between about 70% to about 95% the outer diameter of the proximal segment 742*b* of the second axial face 742. In one embodiment, the distal segment 742*a* of the second axial face 742 may comprise an outer diameter of between about 80% to about 90% the outer diameter of the proximal segment 742*b* of the second axial face 742. In one embodiment, the distal segment 742*a* of the second axial face 742 may comprise an outer diameter of about 85% the outer diameter of the proximal segment 742*b* of the second axial face 742. In one embodiment, the second axial face 742 is configured to operatively engage an axial circumferential collar 832 of the inlet 800 when in the coupled configuration.

In one embodiment, the second projection 728 defines the second luminal segment 746. In one embodiment, the second luminal segment 746 may comprise a similar inner diameter to the first luminal segment 744. In one embodiment, the second luminal segment 746 may comprise a smaller inner diameter than the proximal segment 744*b* and/or distal segment 744*a* of the first luminal segment 744. In one embodiment, the second luminal segment 746 may taper radially inward in the proximal direction. In one embodiment, the walls of the second luminal segment 746 may be substantially parallel to the A-A' axis. In one embodiment, the walls of first luminal segment 744 and the second luminal segment 746 may be substantially parallel to the A-A' axis.

In one embodiment, the medial lumen 710 may be configured to receive the proximal extension 606 of the cannula 600 when in the coupled configuration. The second luminal segment 746 may further comprise the cannula restriction face 752. The cannula restriction face 752 may define a substantially transverse face which may operatively engage the proximal rim 626 of the cannula 600 when in the coupled configuration.

In one embodiment, the proximal section 706 may comprise a first gland head 756, a first gland lip 758, a first gland gate 760 and a slit 766. In one embodiment, the third axial wall 754 may extend axially from the second axial face 742, thereby connecting the second axial face 742 to the first gland head 756. In one embodiment, the first gland head 756 may taper radially outward in the proximal direction.

In one embodiment, the first gland lip 758 may comprise a portion tapered radially inward in the proximal direction from the connection with the first gland head 756. In one embodiment, the first gland lip 758 may define a larger outer diameter than the first gland head 756. In one embodiment, the first gland lip 758 may operatively engage a proximal lumen 812 the inlet 800 when in the coupled configuration.

The first gland gate 760 may extend axially from the first gland lip 758. The first gland gate 760 may comprise a slit 766. The slit 766 may be configured to move from a closed configuration to an open configuration when a sufficient amount of force is applied to the first gland gate 760 in the distal direction, for example, when a syringe male luer 900 operatively engages inlet threaded collar 806 of the inlet 800 (see FIG. 9). In one embodiment, the slit 766 may further prevent the cannula 600 from passing through it when a sufficient amount of force is applied to the first gland gate 760 in the distal direction, for example, when a syringe operatively engages the inlet threaded collar 806 of the inlet 800.

With respect to FIGS. 3 and 7, in one embodiment, upon connection of a syringe to the proximal portion 16 of the infusion device 10, the first gland 700 may compress a distance before the cannula restriction face 752 of the first gland 700 contacts the proximal rim 626 of the cannula 600. In one embodiment, this compression distance is between about 0.003 inches to about 0.018 inches. In one embodiment, this compression distance is between about 0.005 inches to about 0.015 inches. In one embodiment, this compression distance is between about 0.007 inches to about 0.010 inches. In one embodiment, contact of the cannula restriction face 752 with the proximal rim 626 may allow the slit 766 to transition to the open configuration. Transition of the slit 766 to the open configuration may prevent the cannula 600 from protruding through the slit 766.

In one embodiment, the proximal section 706 defines a proximal lumen 712. The proximal lumen 712 may comprise a distal bore 762 and a proximal bore 764. In one embodiment, the proximal bore 764 extends radially outward in the proximal direction from the distal bore 762, such that the proximal bore 764 defines a greater inner diameter than the distal bore 762. For example, in one embodiment, the distal bore 762 may comprise an inner diameter of between about 0.02 inches to about 0.06 inches. In one embodiment, the distal bore 762 may comprise an inner diameter of between about 0.03 inches to about 0.05 inches. In one embodiment, the distal bore 762 may comprise an inner diameter of about 0.04 inches. In one embodiment, the largest inner diameter of the proximal bore 764 may be between about 0.08 inches to about 0.12 inches. In one embodiment, the largest inner diameter of the proximal bore 764 may be between about 0.09 inches to about 0.11 inches. In one embodiment, the largest inner diameter of the proximal bore 764 may be about 0.1 inches.

In one embodiment, the first gland gate 760 comprises a diameter of 0.161 inches, the first gland lip 758 extends axially from the first gland gate 760 about 0.031 inches, the first gland head 756 extends distally from the first gland lip 758 about 0.067 inches, the third axial wall 754 extends axially from the first gland head 756 about 0.013 inches, the second axial face 742 extends axially from the third axial wall 754 about 0.034 inches, the second axial wall 740 extends axially from the second axial face 742 about 0.017 inches, the first projection 726 extends distally from the second axial wall 740 about 0.098 inches, the first axial wall 724 extends axially from the first projection 726 about 0.041 inches, the first gland longitudinal wall 718 extends distally from the first axial wall 724 about 0.035 inches, the proximal face 717 extends axially from the first gland longitudinal wall 718 about 0.009 inches, the first axial face 716 extends axially from the proximal face 717 about 0.041 inches, the distal face 714 extends axially from the first axial face 716 about 0.012 inches, the first distal lumen wall 720 extends proximally from the distal face 714 about 0.011 inches, the wall connector 721 extends axially from the first distal lumen wall 720 about 0.007 inches, the second distal lumen wall 722 extends proximally from the wall connector 721 about 0.042 inches, the medial lumen 710 extends proximally from the second distal lumen wall 722 about 0.135 inches, the cannula restriction face 752 extends axially from the medial lumen 710 about 0.025 inches, the distal bore 762 extends proximally from the cannula restriction face 752 about 0.03 inches, the proximal bore 764 extends proximally from the distal bore 762 about 0.06 inches, and the slit 766 extends proximally from the proximal bore 764 to the first gland gate 760 at a distance of about 0.02 inches.

In some embodiments, the first gland 700 may comprise a resilient and/or compressible material. In one embodiment, the first gland 700 may comprise a synthetic isoprene with silica filler. In one embodiment, the first gland 700 may comprise a synthetic isoprene with silica filler that is free of natural rubber, latex, or mercaptobenzimidazol.

Figure 8:
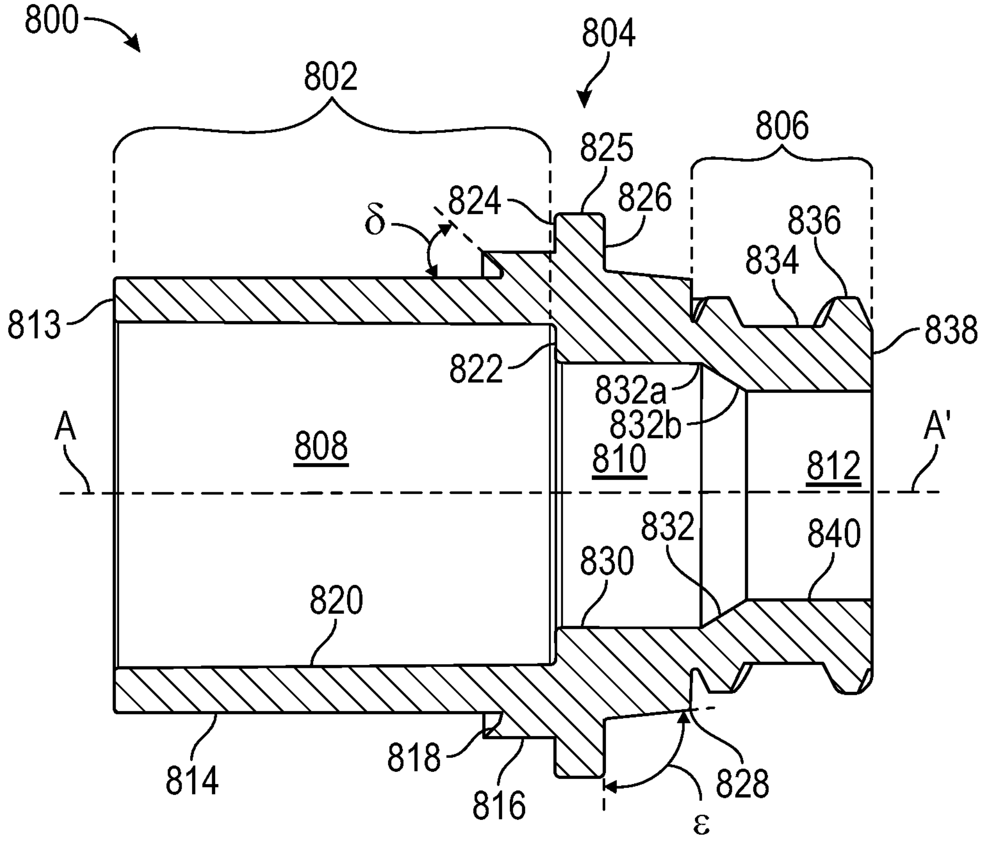
FIG. 8 is a cross-sectional view of an embodiment of the inlet.

Referring to FIG. 8, a cross-sectional view of the inlet 800 is depicted along the plane A-A'. In one embodiment, the inlet 800 may function as an access point for a syringe to the proximal end of infusion device 10. Inlet 800 is configured to receive first gland 700, cannula 600, and a proximal segment 504 of second gland 500 therein. In some embodiments, the entirety of the first gland 700 is received within the inlet 800 and the first gland gate 760 at the proximal end of the first gland 700 is flush with the inlet head 838 at the proximal end of the inlet 800. In some embodiments, the entirety of the cannula 600 is received within a central lumen of the inlet 800. Inlet 800 is also configured to compress the distal segment 502 of the second gland 500 to prevent internal leakage between the second gland 500 and the coupler 400.

The inlet 800 may comprise an inlet flange 802, a medial rib 804, and the inlet threaded collar 806. In one embodiment, the inlet flange 802 may comprise a first exterior wall 814 and a second exterior wall 816 including an inlet swage 818 disposed therebetween. In one embodiment, the first exterior wall 814 defines an outer diameter of between about 0.325 inches to about 0.345 inches. In one embodiment, the first exterior wall 814 defines an outer diameter of between about 0.33 inches to about 0.34 inches. In one embodiment, the first exterior wall 814 defines an outer diameter of about 0.336 inches. In one embodiment, the first exterior wall 814 may define an outer diameter that is smaller than the outer diameter of the second exterior wall 816.

In one embodiment, the first exterior wall 814 may be connected to an internal wall 820 via a housing face 813. In one embodiment, the internal wall 820 defines a distal lumen 808 comprising an inner diameter of between about 0.25 inches to about 0.28 inches. In one embodiment, the internal wall 820 defines a distal lumen 808 comprising an inner diameter of between about 0.26 inches to about 0.27 inches. In one embodiment, the internal wall 820 defines a distal lumen 808 comprising an inner diameter of about 0.268 inches. In one embodiment, the housing face 813 may operatively engage the second gland inlet wall 526 of the second gland 500 when in the coupled configuration. Operative engagement of the housing face 813 and the second gland inlet wall 526 may prevent internal leaking within the infusion device 10 between the second gland 500 and the coupler 400. In one embodiment, the first exterior wall 814 may mechanically engage the inlet housing 432 of the coupler 400 when in the coupled configuration. In one embodiment, the distal lumen 808 is configured to receive the proximal segment 504 of the second gland 500, the distal extension 602 and the medial portion 604 of the cannula 600, and the distal section 702 of the first gland 700.

In one embodiment, the inlet swage 818 may protrude axially from the first exterior wall 814 at an angle delta of between about 40 degrees to about 50 degrees. In one embodiment, the inlet swage 818 may protrude axially from the first exterior wall 814 at an angle delta of between about 42 degrees to about 48 degrees. In one embodiment, the inlet swage 818 may protrude axially from the first exterior wall 814 at an angle delta of about 45 degrees. In one embodiment, the inlet swage 818 may couple to the proximal swage 436 of the coupler 400 when in the coupled configuration. In one embodiment, a welded configuration, or mechanical coupling is achieved by ultrasonically welding the inlet swage 818 to the proximal swage 436 to form a permanent connection therebetween. In one embodiment, the second exterior wall 816 may mechanically engage the proximal inlet housing 434 of the coupler 400 when in the coupled configuration.

The distal lumen 808 may connect to a medial lumen 810 via a first gland face 822. In one embodiment, the first gland face 822 may be configured to operatively engage the first axial wall 724 of the first gland 700 when in the coupled configuration. In one embodiment, the first gland face 822 may extend axially from the internal wall 820 such that the medial lumen 810 defines a smaller inner diameter than the distal lumen 808.

The medial lumen 810 may comprise a longitudinal circumferential collar 830 and an axial circumferential collar 832. The longitudinal circumferential collar 830 may define a substantially cylindrical shape such that the walls are substantially parallel to the A-A' axis. In one embodiment, the longitudinal circumferential collar 830 may define an inner diameter of between about 0.19 inches to about 0.215 inches. In one embodiment, the longitudinal circumferential collar 830 may define an inner diameter of between about 0.2 inches to about 0.21 inches. In one embodiment, the longitudinal circumferential collar 830 may define an inner diameter of about 0.205 inches. In one embodiment, the longitudinal circumferential collar 830 is configured to receive the first projection 726 of the first gland 700.

In one embodiment, the axial circumferential collar 832 extends radially inward in the proximal direction from the longitudinal circumferential collar 830. For example, the distal portion 832*a* of the axial circumferential collar 832 may comprise a larger inner diameter than the proximal portion 832*b* of the axial circumferential collar 832. In one example, the distal portion 832*a* of the axial circumferential collar 832 may comprise a substantially similar inner diameter to the longitudinal circumferential collar 830. In one embodiment, the proximal portion 832*b* of the axial circumferential collar 832 may comprise a similar inner diameter to the proximal lumen 812. In one embodiment, the proximal lumen 812 may comprise a smaller inner diameter than the medial lumen 810. In one embodiment, the medial lumen 810 may comprise a smaller inner diameter than the distal lumen 808. In one embodiment, the axial circumferential collar 832 may operatively engage the second axial face 742 of the first gland 700 when in the coupled configuration.

In one embodiment, the medial rib 804 may comprise a distal wall 824 and a proximal wall 826 including a rib wall 825 disposed therebetween. In one embodiment, the rib wall 825 may define an outer diameter of between about 0.41 inches to about 0.45 inches. In one embodiment, the rib wall 825 may define an outer diameter of between about 0.43 inches to about 0.44 inches. In one embodiment, the rib wall 825 may define an outer diameter of about 0.435 inches. In one embodiment, the distal wall 824 is configured to mechanically engage the proximal rim 438 of the coupler 400 when in the coupled configuration.

In one embodiment, the medial rib 804 may be connected to the inlet threaded collar 806 via an axial wall 828. In one embodiment, the axial wall 828 may extend longitudinally from the proximal wall 826 at an angle epsilon of between about 85 degrees to about 105 degrees. In one embodiment, the axial wall 828 may extend longitudinally from the proximal wall 826 at an angle epsilon of between about 90 degrees to about 100 degrees. In one embodiment, the axial wall 828 may extend longitudinally from the proximal wall 826 at an angle epsilon of about 96 degrees.

In one embodiment, the inlet threaded collar 806 may comprise a threading recess 834 and a threading extension 836. In one embodiment, the inlet threaded collar 806 may be configured to connect to a syringe. In this embodiment, connecting the syringe to the inlet threaded collar 806 may be performed by threadable engagement. In one embodiment, connecting the syringe male luer 900 to the inlet threaded collar 806 causes the coupling apparatus 14 to transition from the closed configuration to the open configuration (see FIG. 9). In one embodiment, removal of the syringe from the inlet threaded collar 806 causes the coupling apparatus 14 to transition from the open configuration to the closed configuration.

In one embodiment, the inlet threaded collar 806 may define the proximal lumen 812. In one embodiment, the proximal lumen 812 may be configured to receive and operatively engage the proximal section 706 of the first gland 700. In one embodiment, the proximal lumen 812 may comprise an inner diameter of between about 0.14 inches to about 0.18 inches. In one embodiment, the proximal lumen 812 may comprise an inner diameter of between about 0.15 inches to about 0.17 inches. In one embodiment, the proximal lumen 812 may comprise an inner diameter of about 0.162 inches.

In one embodiment, the inlet threaded collar 806 extends distally from the inlet head 838 about 0.14 inches, the axial wall 828 extends axially from the inlet threaded collar 806 about 0.064 inches, the proximal wall 826 extends axially from the axial wall 828 about 0.041 inches, the rib wall 825 extends distally from the proximal wall 826 about 0.036 inches, the distal wall 824 extends axially from the rib wall 825 about 0.028 inches, the second exterior wall 816 extends distally from the distal wall 824 about 0.053 inches, the inlet swage 818 extends axially from the second exterior wall 816 about 0.022 inches, the first exterior wall 814 extends distally from the inlet swage 818 about 0.293 inches, the housing face 813 extends axially from the first exterior wall 814 about 0.034 inches, the internal wall 820 extends proximally from the housing face 813 about 0.331 inches, the first gland face 822 extends axially from the internal wall 820 about 0.029 inches, the longitudinal circumferential collar 830 extends proximally from the first gland face 822 about 0.107 inches, the axial circumferential collar 832 extends axially from the longitudinal circumferential collar 830 about 0.04 inches, and the proximal housing wall 840 extends proximally from the axial circumferential collar 832 about 0.095 inches.

In some embodiments, the inlet 800 may comprise an elastomeric medical grade synthetic resin material. In some embodiments, the inlet 800 may comprise a medical grade rigid or semirigid synthetic resinous material suitable for supporting an operable connection, such as, for example, polyvinyl chloride or polycarbonate. In some embodiments, the inlet 800 comprises clear polycarbonate to allow for a clear view of the fluid path of the device. In some embodiments, inlet 800 is received within the coupler 400 and can be ultrasonically welded thereto.

Figure 9:
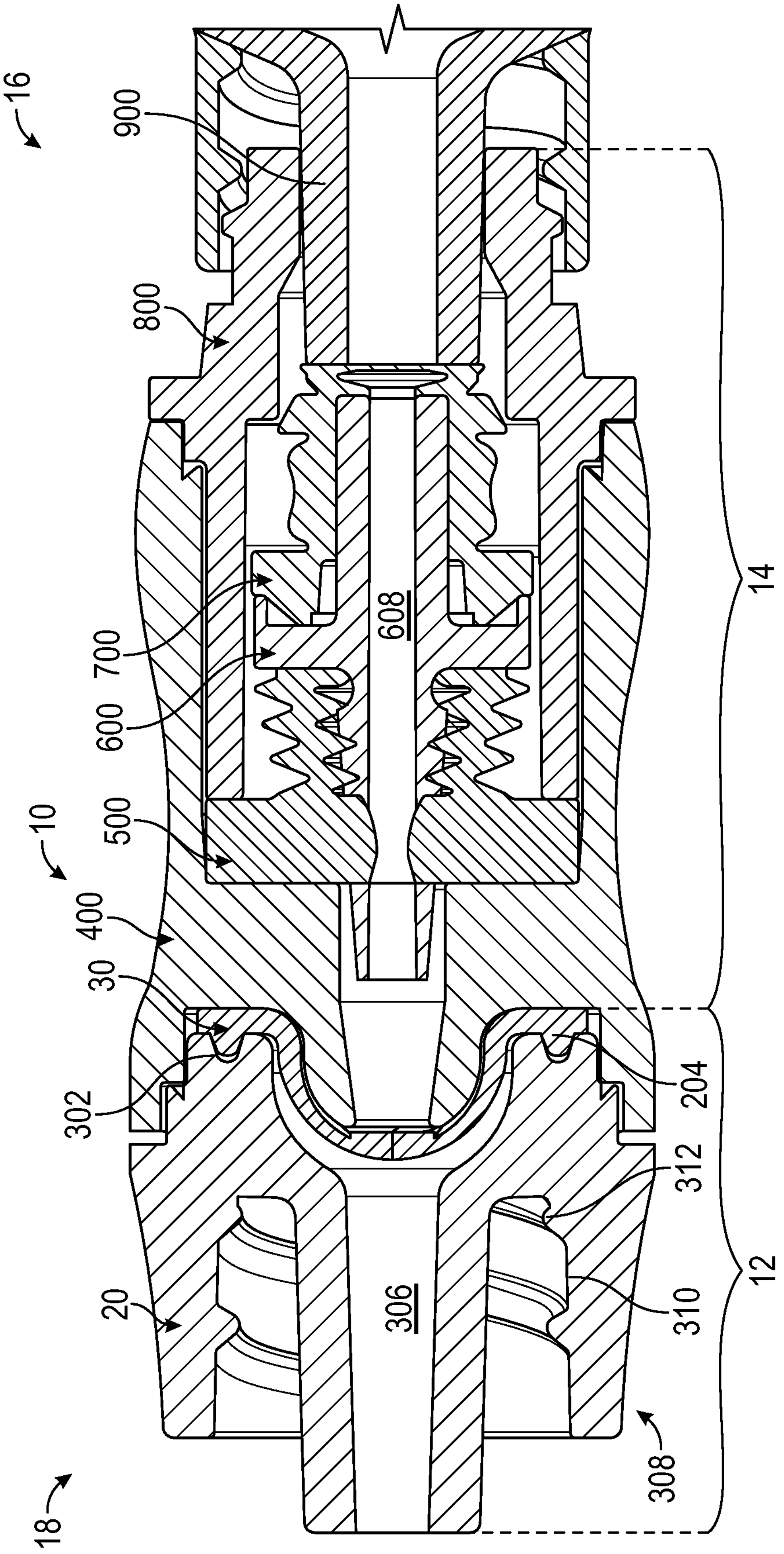
FIG. 9 is a cross-sectional view of an open configuration of the valve assembly of FIGS. 1-3, according to some embodiments.

Referring now to FIG. 9, infusion device 10 is depicted, according to some embodiments, in the open configuration (i.e., operatively attached to a syringe male luer 900 at the inlet 800). As depicted and described above, when syringe male luer 900 is attached to inlet 800, a portion of the syringe male luer 900 compresses first gland 700. Note that the proximal section 706 of the first gland 700 may be substantially compressed by the syringe male luer 900. Additionally, first gland 700 is distally displaced by the syringe male luer 900 (compare FIG. 9 to FIG. 3). Compression of first gland 700 may cause opening of slit 766, allowing the passage of fluid therethrough. FIG. 9 further illustrates distal displacement of cannula 600. Displacement of cannula 600 may cause compression of second gland 500 while also allowing distal extension 602 to be displaced therethrough. The plurality of circumferential protrusions 530, 506, 508, 510 and plurality of circumferential recesses 512, 514, 516 allow for compression of the proximal segment of the second gland 500. Additionally, the distal segment 502 is substantially stabilized by engaging the housing face 813, proximal axial wall 430, and gland wall 428. Displacement of the distal extension 602 through the distal cannula lumen 520 creates a friction fit between the cannula restriction wall 522 and the cannula axial wall 610. Such a friction fit prevents passing fluid from exiting the central lumen 608. It is also noted that inlet 800 and coupler 400 are not displaced or biased by insertion of syringe male luer 900, therein providing a rigid structure by which first gland 700, cannula 600, and second gland 500 move within.

Features described above as well as those claimed below may be combined in various ways without departing from the scope hereof. The following examples illustrate some possible, non-limiting combinations:

(A1) A coupling apparatus configured to connect a syringe to a patient via a valve assembly for infusion of fluids, the coupling apparatus comprising: an inlet having an inlet flange, a medial rib, a collar, and a central lumen; a first gland having a distal section, a medial section, and a proximal section; a cannula having a distal extension, a medial portion, a proximal extension, and a central lumen therethrough, the proximal extension of the cannula being received within both the distal section and the medial section of the first gland; a second gland having a distal segment, a proximal segment, and a proximal cannula lumen, the proximal cannula lumen receiving the distal extension of the cannula, wherein the inlet receives the first gland, the entire cannula, and the proximal segment of the second gland within the central lumen; and a coupler having a central bore receiving the second gland and the inlet flange of the inlet.

(A2) For the coupling apparatus denoted as (A1), the distal section of the first gland comprises a distal face abutting the medial portion of the cannula.

(A3) For the coupling apparatus denoted as (A1) or (A2), the proximal segment of the second gland comprises an axial wall abutting the medial portion of the cannula.

(A4) For the coupling apparatus denoted as any of (A1) through (A3), the distal segment of the second gland abuts an axial wall of the coupler.

(A5) For the coupling apparatus denoted as any of (A1) through (A4), a proximal end of the coupler abuts the medial rib of the inlet.

(A6) For the coupling apparatus denoted as any of (A1) through (A5), the proximal segment of the second gland comprises a plurality of circumferential protrusions.

(A7) For the coupling apparatus denoted as any of (A1) through (A6), the first gland and the second gland are compressible.

(A8) For the coupling apparatus denoted as any of (A1) through (A7), the inlet flange abuts an axial wall of the distal segment of the first gland.

(B1) A system for controlling flow of liquids to and from a patient, comprising a valve assembly and a coupling apparatus, the valve assembly comprising a male luer lock fitting and a flow control valve; the coupling apparatus including: an inlet, a first gland, a cannula, a second gland, and a coupler, the inlet comprising an inlet flange defining a central lumen, wherein the first gland, the cannula, and a proximal segment of the second gland are all received within the central lumen; the first gland comprising a distal section and a proximal section, wherein the distal section operatively engages a proximal extension of the cannula, and the proximal section operatively engages the inlet; the second gland comprising a distal segment and the proximal segment, wherein the distal segment operatively engages a proximal flange of the coupler, and the proximal segment operatively engages a distal extension of the cannula; and the coupler comprises a distal flange and the proximal flange, wherein the distal flange is mechanically coupled to the male luer lock fitting, and the proximal flange is mechanically coupled to the inlet.

(B2) For the system denoted as (B1), the valve assembly and the coupling apparatus define a lumen that provides a flow path for liquids.

(B3) For the system denoted as (B1) or (B2), the cannula comprises an axial wall that tapers radially outward in a proximal direction.

(B4) For the system denoted as any of (B1) through (B3), the proximal section of the first gland operatively engages the central lumen of the inlet.

(B5) For the system denoted as any of (B1) through (B4), the coupling apparatus comprises an open configuration allowing flow therethrough and a closed configuration preventing intrusion of contaminants therein, the first gland and the second gland being compressed in the open configuration.

(B6) For the system denoted as any of (B1) through (B5), the cannula further comprises a medial portion, and the medial portion operatively engages the proximal segment of the second gland and the distal section of the first gland.

(C1) An infusion device configured to connect a syringe to a patient via a valve assembly, the infusion device comprising: an inlet, a compressible first gland, a cannula, a compressible second gland, and a coupler, the first gland, the cannula, and the second gland are all received within a proximal flange of the coupler and within the inlet, the inlet providing a rigid structure for limiting lateral displacement of the first gland when compressed, the cannula is received by the first gland and the second gland and is distally displaced upon compression of the first gland, and the proximal flange of the coupler mechanically engages the inlet and the second gland.

(C2) For the infusion device denoted as (C1), the second gland comprises a distal segment, the coupler comprises a distal axial wall and a gland wall, and the inlet comprises a housing face, the distal axial wall, the gland wall, and the housing face are configured to stabilize the distal segment of the second gland during compression.

(C3) For the infusion device denoted as (C1) or (C2), a distal extension of the cannula is received within the second gland and wherein a proximal extension of the cannula is received within the first gland.

(C4) For the infusion device denoted as (C3), the distal extension of the cannula includes a cannula recess configured to receive a cannula collar of the second gland.

(C5) For the infusion device denoted as any of (C1) through (C4), wherein the cannula comprises a first gland swage configured to receive a distal face and a first axial face of the first gland.

(C6) For the infusion device denoted as any of (C1) through (C5), wherein the second gland comprises a plurality of circumferential recesses and a plurality of circumferential protrusions, the circumferential recesses and the circumferential protrusions configured to bias the cannula in a proximal direction.

Although the invention has been described with reference to the embodiments illustrated in the attached drawing figures, it is noted that equivalents may be employed and substitutions made herein without departing from the scope of the invention as recited in the claims.

What is claimed is:

1. An infusion device for delivery of fluids from a syringe to a patient, comprising:

an inlet having an inlet proximal end and an inlet distal end, the inlet proximal end configured to receive the syringe;

a luer lock fitting housing a flow control valve, the luer lock fitting defining a first lumen within the infusion device; and a coupler having a coupler proximal end coupled to the inlet distal end and a coupler distal end coupled to the luer lock fitting;

a proximal gland;

a distal gland;

a cannula received within the proximal gland and the distal gland, wherein the proximal gland, the distal gland, and the cannula are at least partially housed within the inlet and the coupler, wherein the proximal gland, the distal gland, and the cannula are fluidly connected and define a second lumen within the infusion device, and wherein the first lumen and the second lumen are fluidly connected, defining a central fluid passageway through the infusion device for the delivery of fluids from the syringe to the patient.

2. The infusion device of claim 1, wherein the proximal gland comprises a proximal end comprising a self-opening slit configured to prevent proximal movement of the cannula out of the proximal gland.

3. The infusion device of claim 2, wherein the self-opening slit opens responsive to a force from the syringe being inserted into the inlet.

4. The infusion device of claim 3, wherein when the force is applied, an interior face of the proximal gland is forced distally to abut against a proximal face of the cannula whereupon the self-opening slit opens.

5. The infusion device of claim 1, wherein the cannula is a dual barb cannula having an upper barb and a lower barb.

6. The infusion device of claim 5, wherein the upper barb comprises a recessed wall configured to receive a distal end of the proximal gland therein when the proximal gland is compressed by the syringe, and wherein the lower barb comprises a locking notch for retaining the cannula on the distal gland.

7. The infusion device of claim 1, wherein the proximal gland, the distal gland, and the cannula are movable within the coupler and the inlet when the syringe is inserted.

8. A system for controlling flow of liquids to and from a patient via a fluid delivery device, comprising:

a valve assembly comprising a luer lock fitting and a flow control valve, wherein the valve assembly defines a first fluid path; and a coupling assembly for coupling the valve assembly to the fluid delivery device, comprising:

an outer assembly, comprising:

an inlet configured to receive the fluid delivery device; and a coupler coupled to the inlet at a proximal end and to the luer lock fitting at a distal end; and an inner assembly housed within the outer assembly, comprising:

an upper gland;

a lower gland; and a cannula received within the upper gland and the lower gland, wherein the upper gland, the lower gland, and the cannula are fluidly coupled, defining a second fluid path, and wherein the second fluid path is fluidly coupled to the first fluid path.

9. The system of claim 8, wherein the flow control valve is configured to selectively open to allow bidirectional fluid flow between the first fluid path and the second fluid path.

10. The system of claim 8, wherein the lower gland comprises a tapered through hole configured to create a seal when the cannula passes through the tapered through hole upon insertion of the fluid delivery device into the inlet.

11. The system of claim 10, wherein the lower gland is configured to return to an original position when the fluid delivery device is removed from the coupling assembly.

12. The system of claim 10, wherein the coupler comprises a bore having a proximal bore portion and a distal bore portion, the proximal bore portion having a larger diameter than the distal bore portion, and wherein the distal bore portion is configured to receive the tapered through hole of the lower gland when the fluid delivery device is inserted into the inlet.

13. The system of claim 8, wherein the coupler comprises a proximal flange for mechanically connecting to the inlet and a distal flange for mechanically coupling to the luer lock fitting.

14. The system of claim 13, wherein the distal flange comprises a valve wall that operatively engages the flow control valve, and wherein the coupler further comprises a protrusion disposed proximal to the distal flange, the protrusion configured to prevent collapse of the flow control valve when a pressure is applied to a distal side of the flow control valve.

15. A coupling assembly for connecting a flow control assembly to a syringe, the coupling assembly comprising:

an inlet having an inlet proximal end for receiving the syringe and an inlet distal end;

a coupler having a coupler proximal end coupled to the inlet distal end and a coupler distal end coupled to the flow control assembly;

an upper gland;

a lower gland; and a displaceable cannula having a proximal barb received within the upper gland and a distal barb received within the lower gland, wherein the upper gland, the lower gland, and the displaceable cannula are at least partially housed within the inlet and the coupler; and a straight, unaltered fluid path extending through the upper gland, the displaceable cannula, and the lower gland, wherein the straight, unaltered fluid path is configured to be fluidly connected to the flow control assembly, thereby providing a fluid passageway between the syringe and the flow control assembly, and wherein the straight, unaltered fluid path is maintained when the displaceable cannula is displaced.

16. The coupling assembly of claim 15, wherein the distal barb of the displaceable cannula comprises a recessed locking notch, and wherein the lower gland comprises a collar that couples with the recessed locking notch to retain the lower gland on the displaceable cannula.

17. The coupling assembly of claim 16, wherein the lower gland comprises a first lumen therethrough, the first lumen comprising a proximal lumen portion having a variable diameter that varies along a longitudinal axis of the coupling assembly, and wherein the variable diameter is configured to bias the displaceable cannula to a nominal position when the syringe is not inserted in the coupling assembly.

18. The coupling assembly of claim 15, wherein the lower gland comprises a distal flange, wherein the inlet is configured to compress the distal flange to prevent fluid leakage out of the lower gland.

19. The coupling assembly of claim 15, wherein the displaceable cannula further comprises a medial portion between the distal barb and the proximal barb, and wherein the medial portion comprises a recessed region configured to receive a distal wall of the upper gland.

20. The coupling assembly of claim 15, wherein the upper gland and the lower gland, are compressible, wherein when the syringe is inserted into the inlet, the upper gland and the lower gland are compressed and the displaceable cannula is displaced distally while maintaining both the straight, unaltered fluid path and the fluid connection to the flow control assembly.

* * * * *